United States Patent
Porter

(10) Patent No.: US 8,540,759 B2
(45) Date of Patent: Sep. 24, 2013

(54) STENT DELIVERY CATHETER WITH RAPID EXCHANGE CAPABILITIES

(75) Inventor: Stephen C. Porter, Oakland, CA (US)

(73) Assignees: Stryker Corporation, Kalamazoo, IN (US); Stryker NV Operations Limited, Dublin (IE)

( * ) Notice: Subject to any disclaimer, the term of this patent is extended or adjusted under 35 U.S.C. 154(b) by 133 days.

(21) Appl. No.: 13/277,730

(22) Filed: Oct. 20, 2011

(65) Prior Publication Data
US 2012/0101561 A1 Apr. 26, 2012

Related U.S. Application Data

(60) Provisional application No. 61/394,935, filed on Oct. 20, 2010.

(51) Int. Cl.
*A61F 2/82* (2013.01)
(52) U.S. Cl.
USPC .......................................... 623/1.11; 606/108
(58) Field of Classification Search
USPC .................. 606/108; 623/1.11, 1.12, 1.23
See application file for complete search history.

(56) References Cited

U.S. PATENT DOCUMENTS

| | | | |
|---|---|---|---|
| 4,580,568 A | 4/1986 | Gianturco | |
| 4,768,507 A | 9/1988 | Fischell et al. | |
| 5,026,377 A | 6/1991 | Burton et al. | |
| 5,364,376 A | 11/1994 | Horzewski et al. | |
| 5,534,007 A | 7/1996 | St. Germain et al. | |
| 5,690,644 A | 11/1997 | Yurek et al. | |
| 5,702,418 A | 12/1997 | Ravenscroft | |
| 5,743,874 A | 4/1998 | Fischell et al. | |
| 6,019,778 A | 2/2000 | Wilson et al. | |
| 6,165,167 A | 12/2000 | Delaloye | |
| 6,254,609 B1 | 7/2001 | Vrba et al. | |
| 6,592,549 B2 | 7/2003 | Gerdts et al. | |
| 6,689,144 B2 | 2/2004 | Gerberding | |
| 6,890,317 B2 | 5/2005 | Gerdts et al. | |
| 7,115,109 B2 | 10/2006 | Gerdts et al. | |
| 7,468,053 B2 | 12/2008 | Gerdts et al. | |
| 7,527,643 B2 | 5/2009 | Case et al. | |
| 7,776,080 B2 | 8/2010 | Bei et al. | |

(Continued)

FOREIGN PATENT DOCUMENTS

| | | |
|---|---|---|
| WO | 94/01164 | 1/1994 |
| WO | 94/03213 | 2/1994 |

OTHER PUBLICATIONS

PCT International Search Report and Written Opinion for International Patent Application No. PCT/US2011/057067, Applicant Stryker Corporation, forms PCT/ISA/220, 210, and 237, mailed on Jan. 31, 2012 (10 pages).

*Primary Examiner* — Ryan Severson
(74) *Attorney, Agent, or Firm* — Vista IP Law Group LLP

(57) ABSTRACT

A stent delivery system having rapid exchange capabilities for delivering a self-expandable stent. The system includes a delivery catheter and a sheath positionable in the lumen of the delivery catheter. The delivery catheter includes an elongate shaft extending distally from a hub assembly. The elongate shaft includes a lumen extending therethrough and a guidewire port providing access to the lumen at a location intermediate the proximal and distal ends of the elongate shaft. The sheath is positionable in the lumen of the delivery catheter such that the sheath extends across the guidewire port to close off the guidewire port to allow a stent to be passed through the sheath from proximal of the guidewire port to distal of the guidewire port.

14 Claims, 20 Drawing Sheets

(56) References Cited

U.S. PATENT DOCUMENTS

| | | |
|---|---|---|
| 7,789,860 B2 | 9/2010 | Brady et al. |
| 7,815,601 B2 | 10/2010 | Jordan et al. |
| 7,867,271 B2 | 1/2011 | Geiser et al. |
| 2003/0233117 A1 | 12/2003 | Adams et al. |
| 2006/0263145 A1 | 11/2006 | Pal |
| 2008/0009934 A1 | 1/2008 | Schneider et al. |
| 2009/0036967 A1 | 2/2009 | Cummings |
| 2009/0105808 A1 | 4/2009 | Gerdts et al. |
| 2009/0182200 A1 | 7/2009 | Golden et al. |
| 2010/0125322 A1 | 5/2010 | Fitzgerald et al. |
| 2010/0168756 A1 | 7/2010 | Dorn et al. |
| 2010/0174355 A1 | 7/2010 | Boyle et al. |

STENT DELIVERY CATHETER WITH RAPID EXCHANGE CAPABILITIES

RELATED APPLICATION DATA

The present application claims the benefit under 35 U.S.C. §119 to U.S. provisional patent application Ser. No. 61/394,935, filed Oct. 20, 2010. The foregoing application is hereby incorporated by reference into the present application in its entirety

TECHNICAL FIELD

The disclosure is directed to delivery systems for delivering endoprosthesis devices such as stents, with a delivery catheter having rapid exchange capabilities. More particularly, the disclosure is directed to stent delivery systems utilizing a rapid-exchange delivery catheter for delivering a stent to a target location in a body lumen.

BACKGROUND

Stents are generally cylindrically shaped devices configured to hold open and/or expand a segment of a blood vessel or other body lumen. For example, a stent may be used to maintain the patency of a body lumen, such as a blood vessel, subsequent to a percutaneous transluminal angioplasty (PTA) or percutaneous transluminal coronary angioplasty (PTCA) procedure, or other procedure used to open an obstructed body lumen.

One type of stent, known as self-expanding stents, are configured to be delivered in an elastically compressed state while being confined within a tubular restraining member, and then allowed to elastically expand into engagement with the interior of the body lumen when removed from the tubular restraining member.

One embodiment of a catheter delivery system is the so-called "over-the-wire" delivery system, in which a catheter is introduced into the patient over a guide wire which has been previously introduced. In this embodiment, the guidewire extends through the entire length of the catheter through a lumen of the catheter. Another embodiment of a catheter delivery system is the so-called "rapid-exchange" delivery system, in which the guidewire extends through only a distal portion of the catheter from the distal tip to a guidewire port located proximal of the distal tip.

Prior art "over-the-wire" stent delivery systems for delivering self-expanding stents may be undesirable as such systems lack the capability to be rapidly advanced over a guidewire and/or exchanged for another delivery system during a medical procedure in a rapid-exchange manner. Furthermore, such over-the-wire systems require the use of a longer wire for exchanges than a rapid exchange system. Some such systems are disclosed in U.S. Pat. Nos. 6,019,778; 5,702,418; 5,026,377; and 4,580,568, the disclosures of which are incorporated herein by reference.

Prior art "rapid-exchange" stent delivery systems for delivering self-expanding stents require the stent to be pre-loaded in the delivery catheter distal of the guidewire port prior to being inserted into the body of the patient such that the guidewire extends through the stent or a separate lumen of the catheter, thus reducing the flexibility and/or maneuverability of the distal portion of the delivery catheter. Some such systems is are disclosed in U.S. Pat. Nos. 7,527,643; 7,468,053 and 5,690,644 and U.S. Pat. Pub. Nos. 2005/0113902, 2009/0105808, and 2010/0125322, the disclosures of which are incorporated herein by reference.

There is a need to provide a stent delivery system for delivering a self-expanding stent to a target location utilizing a delivery catheter having rapid-exchange capabilities for gaining access to a target location yet providing empty lumen capabilities for delivering a stent to the target location through the lumen of the delivery catheter.

SUMMARY

The disclosure is directed to several alternative designs, materials and methods of manufacturing medical device structures and assemblies.

Accordingly, one illustrative embodiment is a stent delivery system including a delivery catheter and a sheath positionable in the lumen of the delivery catheter. The delivery catheter includes an elongate shaft extending distally from a hub assembly. The elongate shaft includes a lumen extending therethrough from a proximal end of the elongate shaft to a distal end of the elongate shaft. The elongate shaft includes a guidewire port providing access to the lumen at a location intermediate the proximal and distal ends of the elongate shaft. The sheath is positionable in the lumen of the delivery catheter such that the sheath extends across the guidewire port to close off the guidewire port to allow a stent to be passed through the sheath from proximal of the guidewire port to distal of the guidewire port. In some instances, the stent delivery system may further include a guidewire configured to extend through the lumen of the elongate shaft between the guidewire port and the distal end of the elongate shaft, and external of the elongate shaft proximal of the guidewire port, and a delivery wire having a stent disposed on a distal portion thereof configured to be passed through the sheath from proximal of the guidewire port to distal of the guidewire port into the lumen of the elongate shaft. The guidewire may be withdrawn from the lumen of the elongate shaft prior to advancing the sheath past the guidewire port and/or passing the stent through the sheath into the lumen of the elongate shaft.

Another illustrative embodiment is a stent delivery system having rapid exchange capabilities. The stent delivery system includes a delivery catheter and a sheath positionable in the lumen of the delivery catheter. The delivery catheter includes an elongate shaft extending distally from a hub assembly. The elongate shaft includes a lumen extending therethrough from a proximal end of the elongate shaft to a distal end of the elongate shaft. The elongate shaft includes a guidewire port extending through a sidewall of the elongate shaft at a location intermediate the proximal and distal ends of the elongate shaft to provide access to the lumen for advancement of the delivery catheter over a guidewire extending through the lumen between the guidewire port and the distal end of the elongate shaft and external of the elongate shaft proximal of the guidewire port. The sheath is positionable in the lumen of the delivery catheter such that the sheath extends across the guidewire port to close off the guidewire port when a guidewire is not extending through the lumen and configured to allow a stent to be passed through the sheath from proximal of the guidewire port to distal of the guidewire port into the lumen of the elongate shaft distal of the sheath. In some instances, the stent delivery system may further include a delivery wire having a stent disposed on a distal portion thereof configured to be passed through the sheath from proximal of the guidewire port to distal of the guidewire port into the lumen of the elongate shaft. The guidewire may be withdrawn from the lumen of the elongate shaft prior to advancing the sheath past the guidewire port and/or passing the stent through the sheath into the lumen of the elongate shaft.

Yet another illustrative embodiment is a method of delivering a stent to a target location in a vasculature. The method includes advancing a guidewire through the vasculature to a location proximate an occlusion. A delivery catheter may then be advanced over the guidewire to a location proximate the occlusion such that the guidewire extends through a lumen of the elongate shaft between a distal end of the elongate shaft and guidewire port located distal of a proximal end of the elongate shaft, and external of the elongate shaft proximal of the guidewire port. The guidewire may then be withdrawn from the lumen of the delivery catheter, and then a stent disposed on a portion of a delivery wire may be advanced out of the distal end of the elongate shaft by passing the stent through the lumen of the delivery catheter from a location proximal of the guidewire port to a location distal of the guidewire port.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
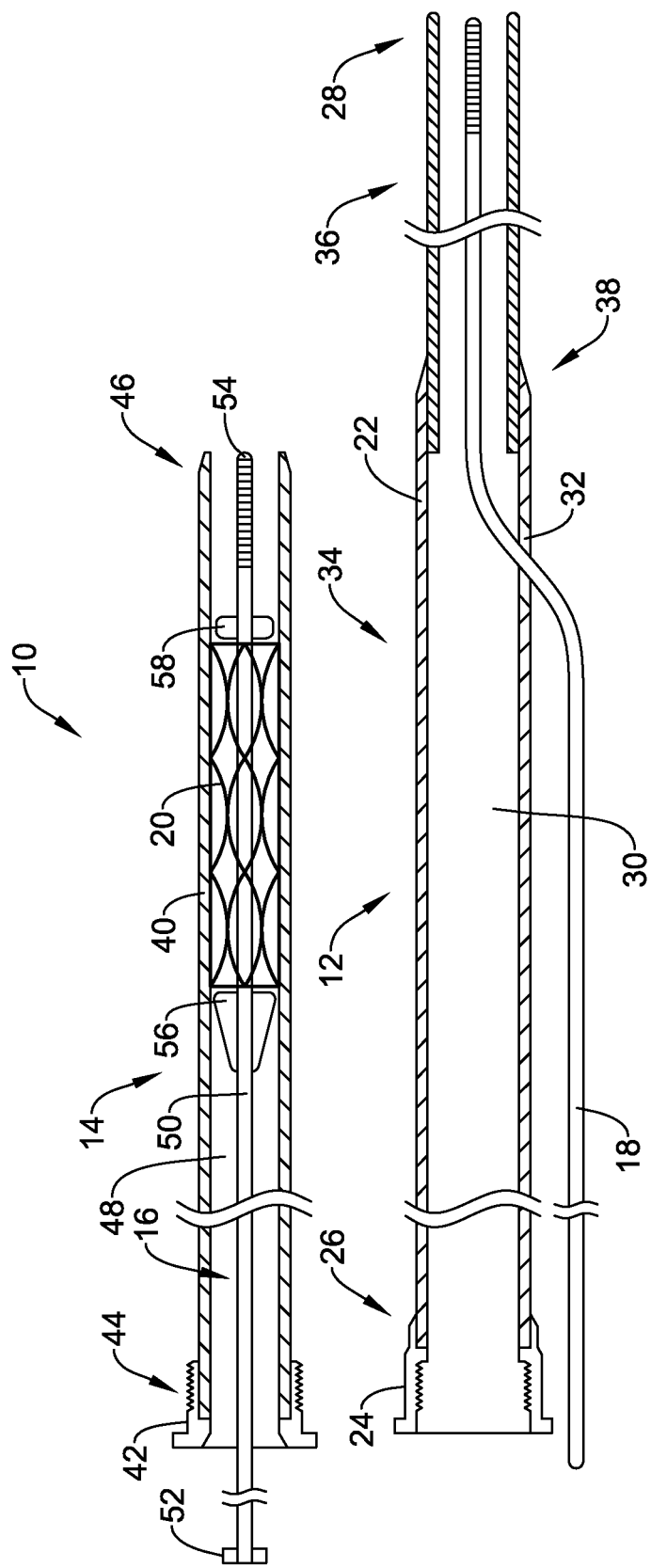
FIG. 1 is a longitudinal cross-sectional view of components of an exemplary stent delivery system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless is clearly stated to the contrary.

Referring now to FIG. 1, there is shown components of an exemplary stent delivery system 10 for delivering a stent, or other prosthetic device to a target location of a body lumen, such as a blood vessel or a biliary duct. The stent delivery system 10 may include a delivery catheter 12, such as a microcatheter dimensioned to reach remote locations of a vasculature, configured to deliver a stent 20 to a target location, such as an occlusion in a blood vessel. The delivery catheter 12 may include an elongate shaft 22 extending distally from a hub assembly 24. The elongate shaft 22 may have a proximal end 26 and a distal end 28, with a lumen 30 extending therethrough in fluid communication with the hub assembly 24. Thus, the lumen 30 may extend the entire length of the delivery catheter 12 from the hub assembly 24 to the distal end 28 of the elongate shaft 22. The delivery catheter 12 may include a single lumen (e.g., only the lumen 30), thus reducing the profile of the delivery catheter 12 relative to catheters having multiple lumens extending therethrough. The lumen 30 may extend axially through the elongate shaft 22 centered along a central longitudinal axis of the elongate shaft 22.

The delivery catheter 12 may include a guidewire port 32 located intermediate the proximal end 26 and the distal end 28 of the elongate shaft 22 providing the delivery catheter 12 with "rapid-exchange" capabilities. The guidewire port 32 may be located a relatively short distance from the distal end 28 and a relatively long distance from the proximal end 26 of the elongate shaft 22 of the delivery catheter 12. In some instances, the elongate shaft 22 may have a length in the range of about 80 cm to about 150 cm, with the guidewire port 32 located about 15 cm to about 35 cm proximal of the distal end 28. The guidewire port 32 may extend through a sidewall of the elongate shaft 22, providing access to the lumen 30 from exterior of the elongate shaft 22. Thus, the delivery catheter 12 may be advanced over a guidewire 18 which extends through the lumen 30 of the elongate shaft 22 between the guidewire port 32 and the distal end 28 of the elongate shaft 22, and external of the elongate shaft 22 proximal of the guidewire port 32 in a rapid exchange manner.

The elongate shaft 22 may include one or more, or a plurality of regions is along the length of the elongate shaft 22 having different configurations and/or characteristics. For example, the elongate shaft 22 may include a proximal portion 34 and a distal portion 36 extending distal of the proximal portion 34. In some embodiments, the distal portion 36 may have an outer diameter less than the outer diameter of the proximal portion 34 to reduce the profile of the distal portion of the elongate shaft 22 and facilitate navigation in tortuous vasculature. Furthermore, the distal portion 36 may be more flexible than the proximal portion 34. The portion of the lumen 30 extending through the proximal portion 34 may be coaxial with the portion of the lumen 30 extending through the distal portion 36. In some instances, the portion of the lumen 30 extending through the proximal portion 34 may have a diameter slightly greater than the diameter of the portion of the lumen 30 extending through the distal portion 36. The elongate shaft 22 may include a transition region 38 between the proximal portion 34 and the distal portion 36. The guidewire port 32 may be located proximal of the transition region 38, thus located in the proximal portion 34 of the elongate shaft 22.

The elongate shaft 22, or portions thereof, may be formed of stainless steel or nickel titanium hypotube, and/or polymeric materials including polyethylene, polyimide, polyethylterpthalate, nylon, polyurethane, fluorinated polymers, elastomeric polyesters and the like. Generally, the more proximal portion 34 may be formed from material that is stiffer than the distal portion 36 so that the proximal portion 34 has sufficient pushability to advance through the patient's vascular system, while the more distal portion 36 may be formed of a more flexible material so that the distal portion 36 may remain flexible and track more easily over the guidewire 18 to access remote locations in tortuous regions of the vasculature. In some instances, the proximal portion 34 may include a reinforcement layer, such a braided layer or coiled layer to enhance the pushability of the delivery catheter 12.

The stent delivery system 10 may also include a sheath, such as an introducer sheath 14 for retaining the stent 20 in a radially compressed configuration for delivery to the target location. The introducer sheath 14 may include an elongate shaft 40 extending distally from a hub assembly 42. The elongate shaft 40 may have a proximal end 44 and a distal end 46, with a lumen 48 extending therethrough in fluid communication with the hub assembly 42. The elongate shaft 40 may be formed of any suitable materials, including those listed above.

The stent delivery system 10 may additionally include a delivery wire 16 extendable through the introducer sheath 14 and delivery catheter 12 for deploying a stent 20 from the distal end 28 of the delivery catheter 12. The delivery wire 16 may include a core wire 50, or other elongate member, extending from a proximal end 52 to a distal end 54. In some instances the distal end 54 may include an atraumatic tip, such as a coil tip or solder tip. The delivery wire 16 may include a proximal bumper 56 and a distal bumper 58 spaced distally from the proximal bumper 56 to allow a stent 20 to be positioned in a radially compressed configuration therebetween. In some instances, the proximal bumper 56 and/or the distal bumper 58 may be coiled members attached to the core wire 50. The delivery wire 16 may be sized to be advanced through the lumen 48 of the introducer sheath 14 and the lumen 30 of the delivery catheter 12 to deploy the stent 20 from the distal end 28 of the delivery catheter 12 at a target location.

The stent 20 may be a self-expanding stent configured to automatically expand from a radially compressed configuration when radially constrained to a radially expanded configuration when unconstrained. The stent 20 may be formed from any number of biocompatible materials, including polymeric materials, metals, and metal alloys, such as stainless steel, tantalum, or a nickel titanium alloy such as a superelastic nickel titanium alloy known as Nitinol.

The stent 20 may be pre-loaded in the introducer sheath 14 between the proximal bumper 56 and the distal bumper 58 of the delivery wire 16 in a radially compressed configuration prior to use with the introducer sheath 14 constraining the stent 20 in the radially compressed configuration. In other embodiments the stent 20 may be pre-loaded in another sheath and then inserted into the introducer sheath 14 during the medical procedure or radially compressed and then inserted into the introducer sheath 14 during the medical procedure.

The stent 20 may be pushed distally through the lumen 48 of the introducer sheath 14 by manipulating the delivery wire 16 such that the proximal bumper 56 contacts the stent 20 and urges the stent 20 distally. If it is desired to pull the stent 20 proximally, the delivery wire 16 may be manipulated proximally such that the distal bumper 58 contacts the stent 20 and urges the stent 20 proximally.

Figure 2:
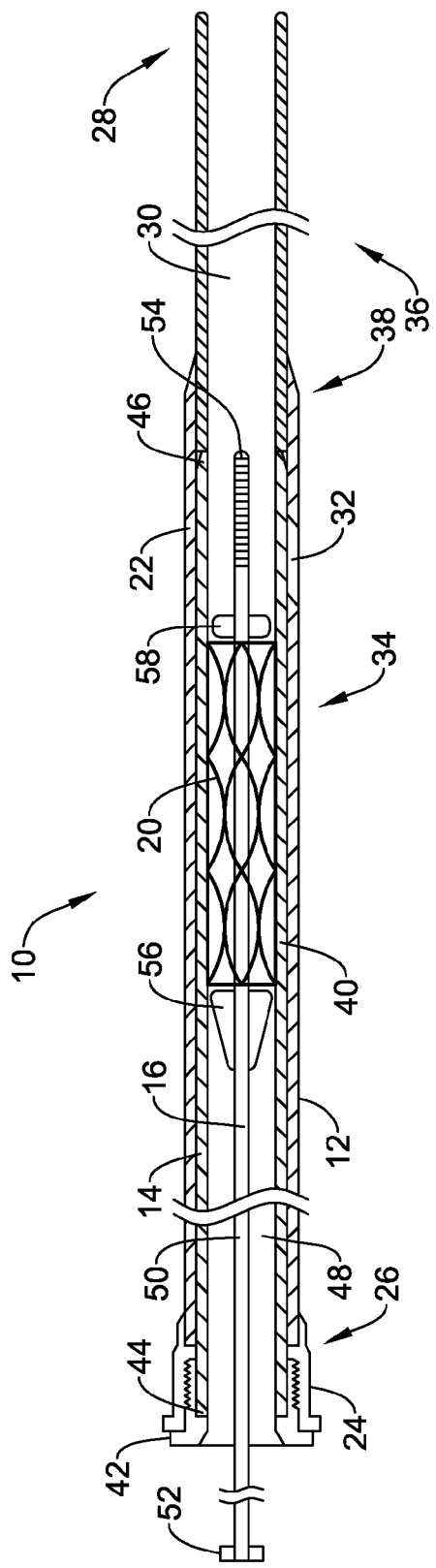
FIG. 2 is a longitudinal cross-sectional view of the components of the exemplary stent delivery system of FIG. 1 in an assembled configuration.

Turning to FIG. 2, the elongate shaft 40 of the introducer sheath 14 may be sized to be inserted into the lumen 30 of the delivery catheter 12 through the hub assembly 24 of the delivery catheter 12. For instance, the introducer sheath 14 may be slidably disposed in the lumen 30 of the delivery catheter 12. The introducer sheath 14 may have a sufficient length such the elongate shaft 40 may be inserted into the lumen 30 of the delivery catheter 12 so that the distal end 46 of the introducer sheath 14 extends distal of the guidewire port 32 of the delivery catheter 12 while a proximal portion of the introducer sheath 14 remains proximal of the delivery catheter 12. Thus, the introducer sheath 14 may extend across the guidewire port 32 to close off the guidewire port 32 to allow the stent 20 to be passed through the introducer sheath 14 from proximal of the guidewire port 32 to distal of the guidewire port 32 without the guidewire port 32 interfering with advancement or retraction of the stent 20 past the guidewire port 32.

The introducer sheath 14 may be sized such that the diameter of the lumen 48 of the introducer sheath 14 is approximately equal to the diameter of the portion of the lumen 30 extending through the distal portion 36 of the delivery catheter 12. Thus, the stent 20 may pass from the lumen 48 of the introducer sheath 14 to the lumen 30 of the delivery catheter 12 without appreciably changing the diameter of the compressed stent 20, providing a smooth transition from the introducer sheath 14 to the delivery catheter 12. Thus, with the introducer sheath 14 positioned in the lumen 30 of the delivery catheter 12, the passageway through the assembly (i.e., the lumen 48 of the introducer sheath 14 continuing into the lumen 30 in the distal portion 36 of the delivery catheter 12 may have a substantially constant diameter throughout.

In some instances, the hub assembly 42 of the introducer sheath 14 may be configured to engage and/or be coupled to the hub assembly 24 of the delivery catheter 12 when the introducer sheath 14 is fully advanced through the lumen 30 such that the distal end 46 of the introducer sheath 14 is positioned distal of the guidewire port 32. For example, as shown in FIG. 2, the hub assembly 42 may include a threaded portion which threadedly engages a threaded portion of the hub assembly 24. In other embodiments, the hub assembly 42 may include an engagement portion which forms an interference fit with an engagement portion of the hub assembly 24, or the hub assembly 42 may include an interlocking portion which interlocks with an interlocking portion of the hub assembly 24 when the introducer sheath 14 is sufficiently advanced in the lumen 30 to close off the guidewire port 32 with the introducer sheath 14. Such configurations may provide an operator with confirmation that the introducer sheath 14 is sufficiently advanced to ensure the introducer sheath 14 is advanced beyond the guidewire port 32 prior to advancing the stent 20 through the delivery system 10.

Furthermore, the elongate shaft 40 of the introducer sheath 14 may be sized such that the distal end 46 of the elongate shaft 40 abuts or contacts the proximal end of the distal portion 36 at the transition region 38 or otherwise contacts a portion of the elongate shaft 22 of the delivery catheter 12 which acts as a stop such that the elongate shaft 40 cannot be advanced further distally. Such a configuration may additionally or alternatively provide an operator with confirmation that the introducer sheath 14 is sufficiently advanced to ensure the introducer sheath 14 is advanced beyond the guidewire port 32 prior to advancing the stent 20 through the delivery system 10. Thus, the introducer sheath 14 may have a length such that a distal portion of the introducer sheath 14 is disposed distal of the guidewire port 32 while at least a portion of the hub assembly 42 of the introducer sheath 14 is located proximal of the hub assembly 24 of the delivery catheter 12.

Figure 3:
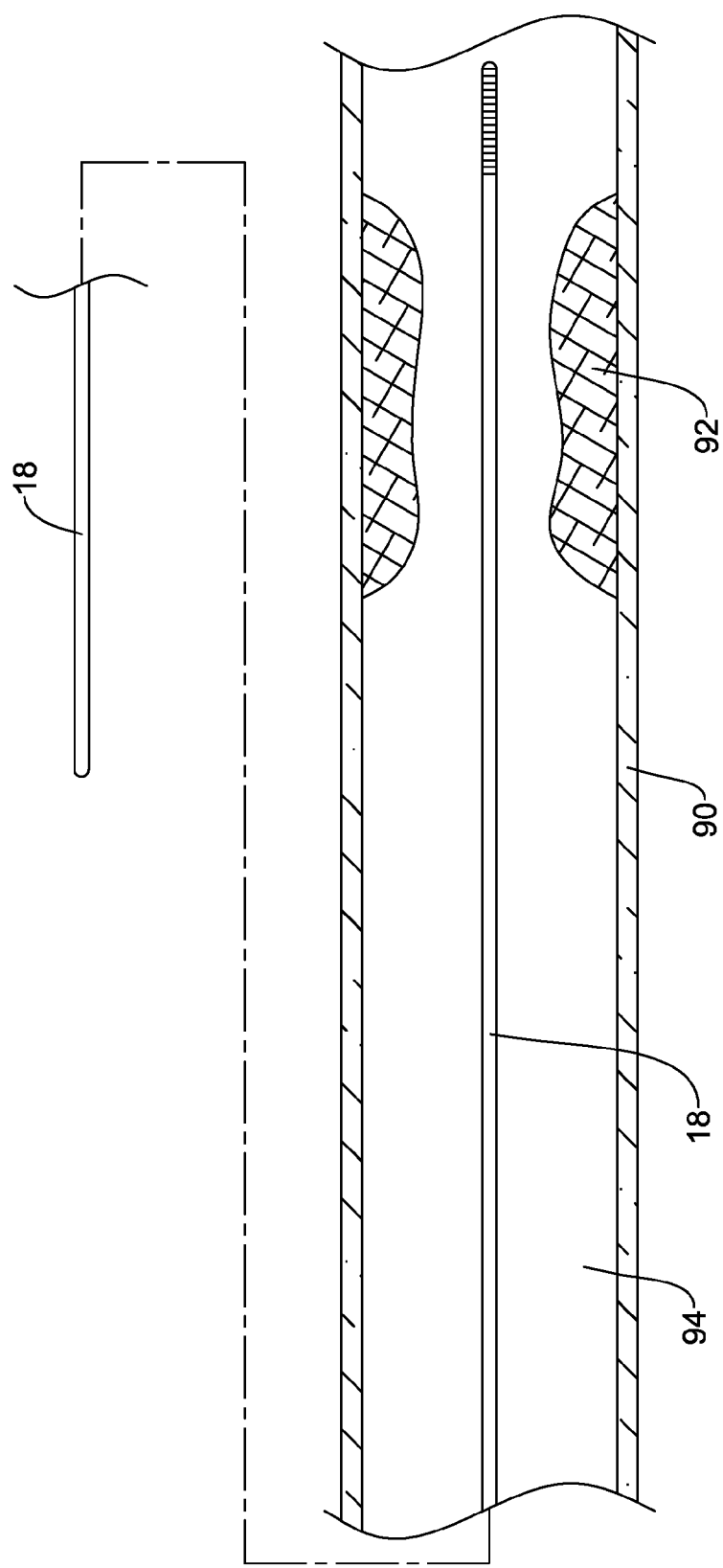
FIGS. 3-7 illustrate an exemplary method of delivering a stent to an occlusion of a body vessel using the stent delivery system of FIGS. 1 and 2.

FIGS. 3-7 illustrate an exemplary method of delivering a stent 20 to an occlusion 92 of a blood vessel 90 using the stent delivery system 10. After gaining access to the vasculature of the patient, as shown in FIG. 3, the guidewire 18 may be advanced through the lumen 94 of the blood vessel 90 to a location proximate the occlusion 92 to establish a pathway along which the delivery catheter 12 may be advanced via the guidewire 18 to position the distal end 28 of the delivery catheter 12 proximate the occlusion 92.

Figure 4:
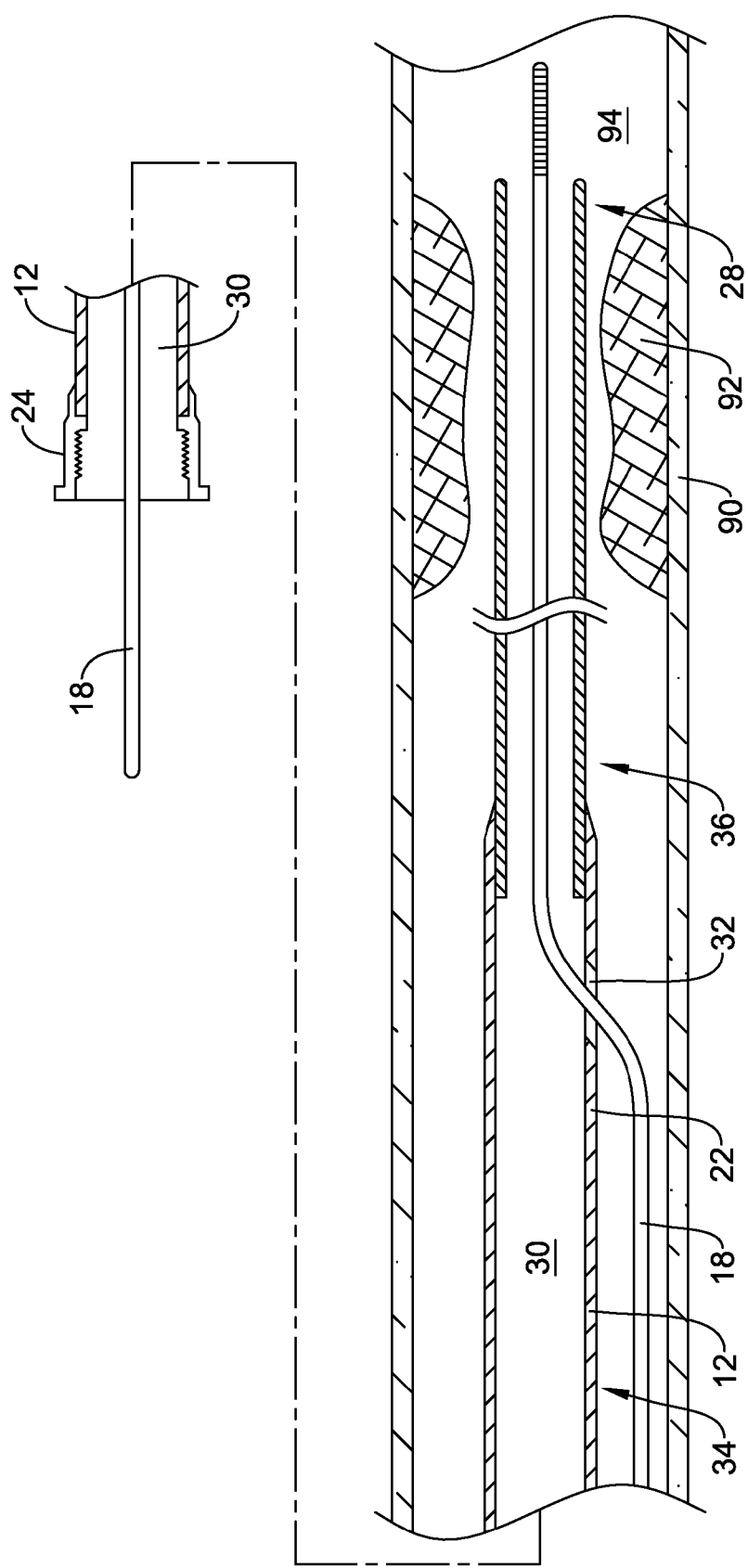

After the guidewire 18 has been positioned, the delivery catheter 12 may be advanced over the guidewire 18 in a rapid exchange manner as shown in FIG. 4. The guidewire 18 may be inserted into the opening of the lumen 30 at the distal end 28 of the delivery catheter 12, through the lumen 30 distal of the guidewire port 32, and exit the delivery catheter through the guidewire port 32. Thus, the guidewire 18 may be routed through the lumen 30 of the delivery catheter 12 throughout the distal portion 36 and exterior of the delivery catheter 12 proximal of the guidewire port 32. In some instances, the lumen 30 of the delivery catheter 12 may not contain the stent 20 while the delivery catheter 12 is being advanced over the guidewire 18 to the occlusion 92.

Figure 5:
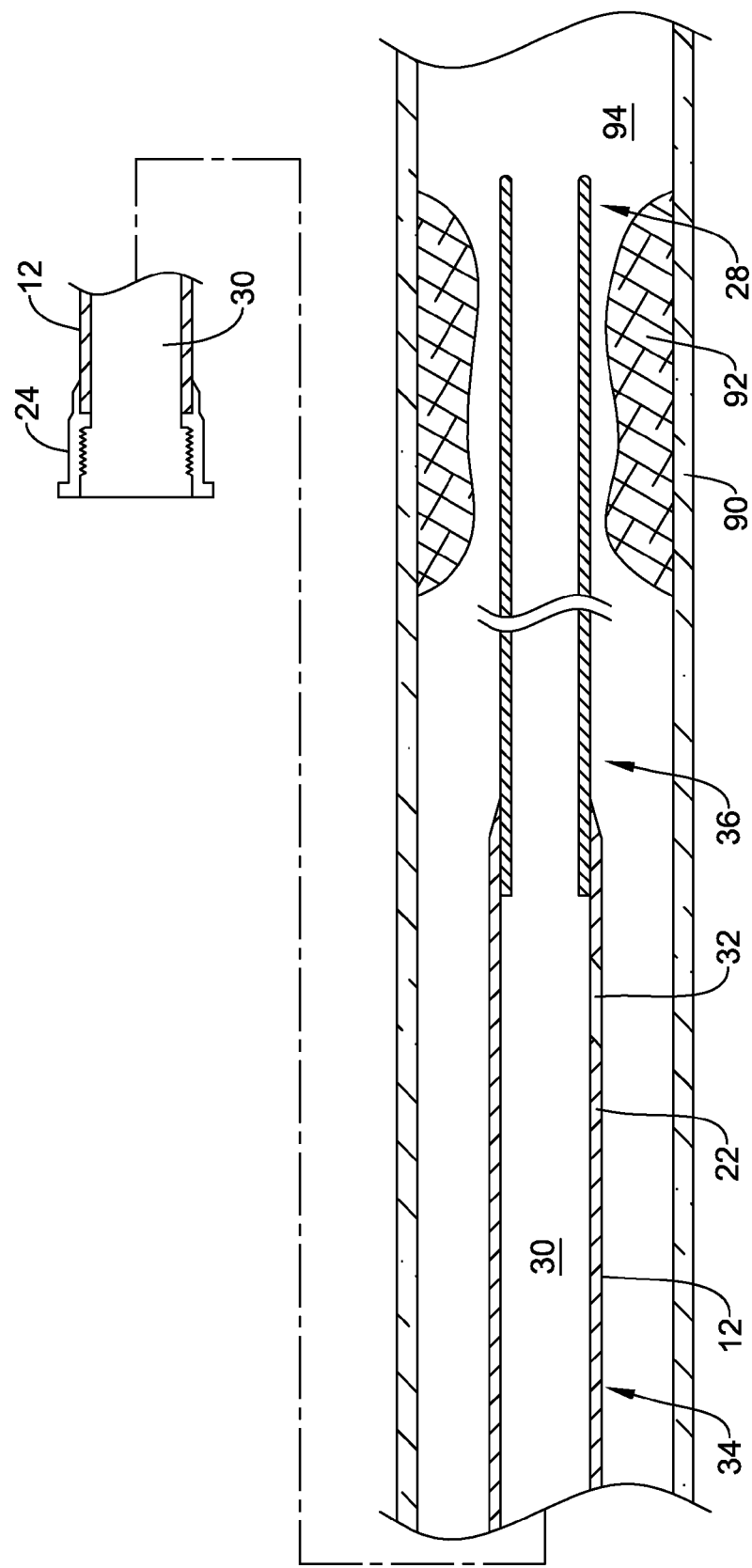

Referring to FIG. 5, once the delivery catheter 12 has been appropriately advanced to the treatment site proximate the occlusion 92, the guidewire 18 may be withdrawn proximally such that the guidewire 18 is no longer positioned in the lumen 30 of the delivery catheter 12. In some instances, the delivery catheter 12 may be advanced distally of the occlusion 92, or cross the occlusion 92, prior to withdrawing the guidewire 18 from the delivery catheter 12. Accordingly, the guidewire 18 may be withdrawn proximally out of the guidewire port 32 to remove the guidewire 18 from the lumen 30. At this point in the procedure, the lumen 30 of the delivery catheter 12 may be empty.

Figure 6:
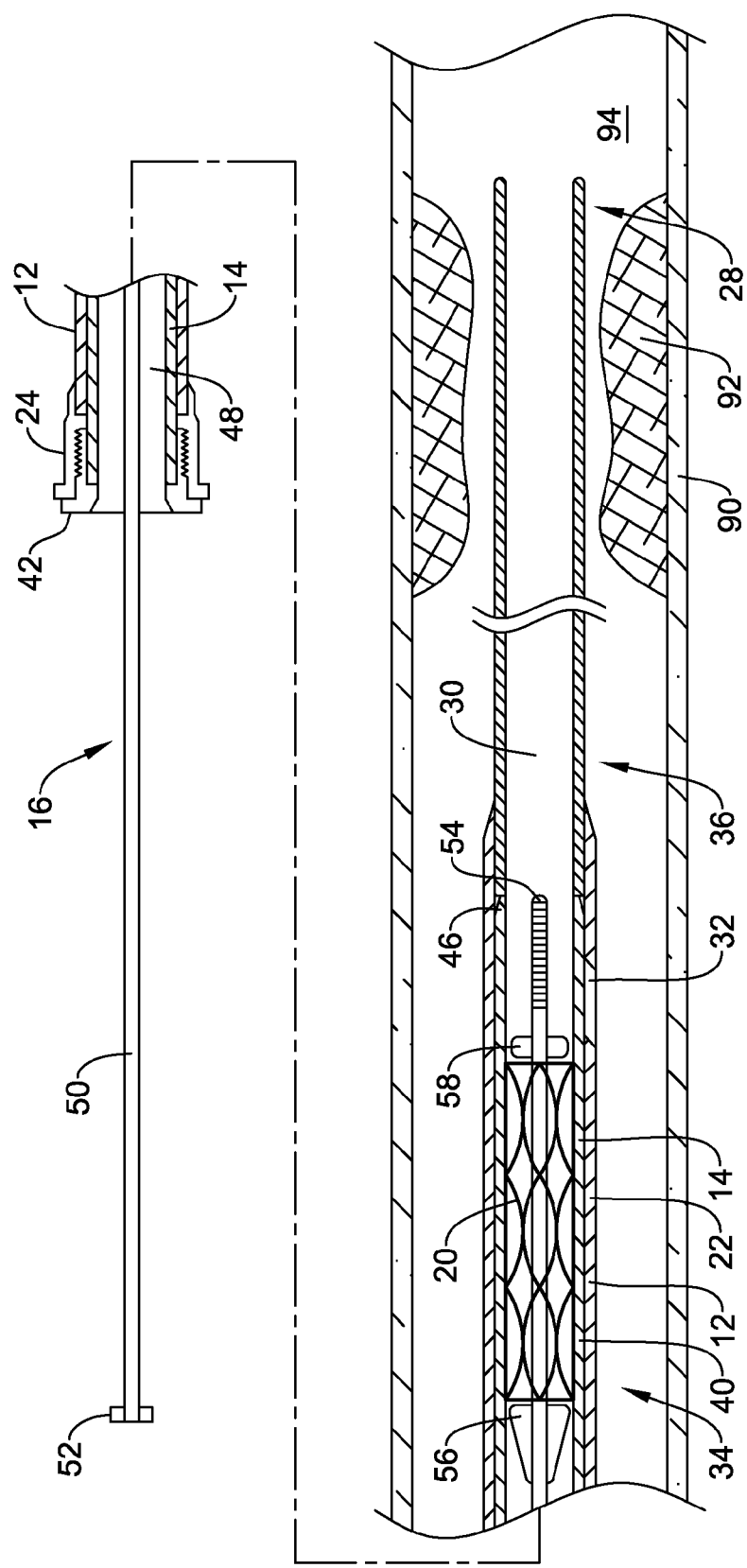

With the guidewire 18 removed from the lumen 30, the introducer sheath 14 may then be advanced into the hub assembly 24 and through the lumen 30 of the delivery catheter 12. As shown in FIG. 6, the introducer sheath 14 may be advanced distally such that the distal end 46 of the introducer sheath 14 passes distally beyond the guidewire port 32 within the lumen 30 to close off the guidewire port 32. The stent 20 may be pre-loaded in the introducer sheath 14, and thus advanced in the introducer sheath 14 as the introducer sheath 14 is advanced through the lumen 30, or the stent 20 may be loaded into the introducer sheath 14 from the proximal end of the introducer sheath 14 after the introducer sheath 14 has been advanced through the lumen 30 and positioned across the guidewire port 32.

Figure 7:
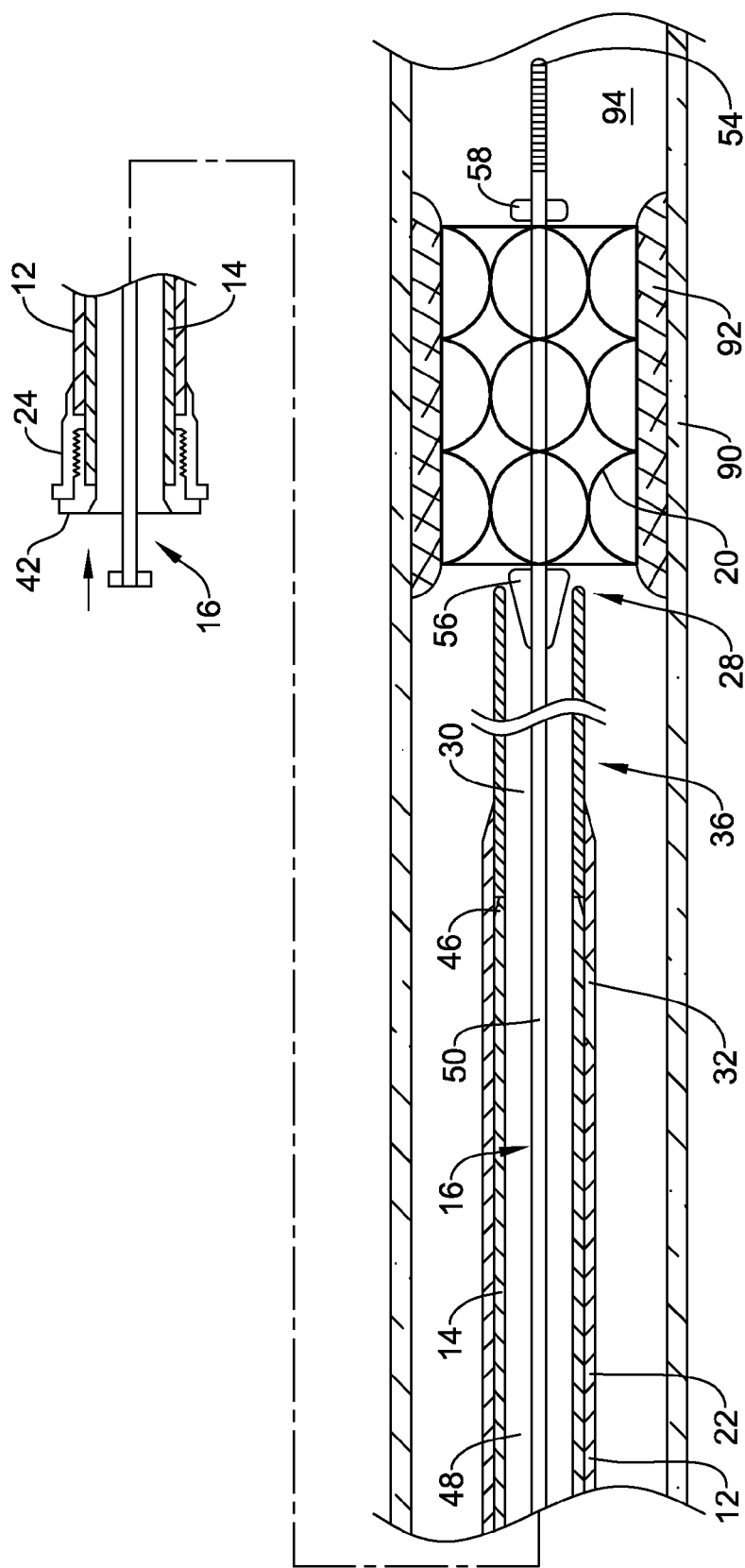

With the introducer sheath 14 positioned across the guidewire port 32, the stent 20 may be advanced distally through the introducer sheath 14 into the lumen 30 of the delivery catheter 12 distal of the introducer sheath 14, and deployed out of the distal end 28 of the delivery catheter 12 at the treatment site as shown at FIG. 7. The stent 20 may be advanced distally by actuating the delivery wire 16 in a distal direction, which causes the proximal bumper 56 to contact the radially compressed stent 20 and urge the stent 20 distally. The stent 20 may pass from the lumen 48 of the introducer sheath 14 to the lumen 30 of the delivery catheter 12 without appreciably changing the diameter of the compressed stent 20, providing a smooth transition from the introducer sheath 14 to the delivery catheter 12. The introducer sheath 14 extends across the guidewire port 32, closing off the guidewire port 32, allowing the stent 20 to be passed through the introducer sheath 14 from a location proximal of the guidewire port 32 to a location distal of the guidewire port 32 without the guidewire port 32 interfering with advancement or retraction of the stent 20 past the guidewire port 32. As the stent 20 exits the distal end 28 of the delivery catheter 12 proximate the occlusion 92, the stent 20 may automatically expand radially outward into engagement with the occlusion 92.

Once the stent 20 has been deployed at the treatment site, the delivery catheter 12, introducer sheath 14 and the delivery wire 16 may be withdrawn from the patient's vasculature, leaving the stent 20 radially expanded at the occlusion 92 in the blood vessel 90.

Figure 8:
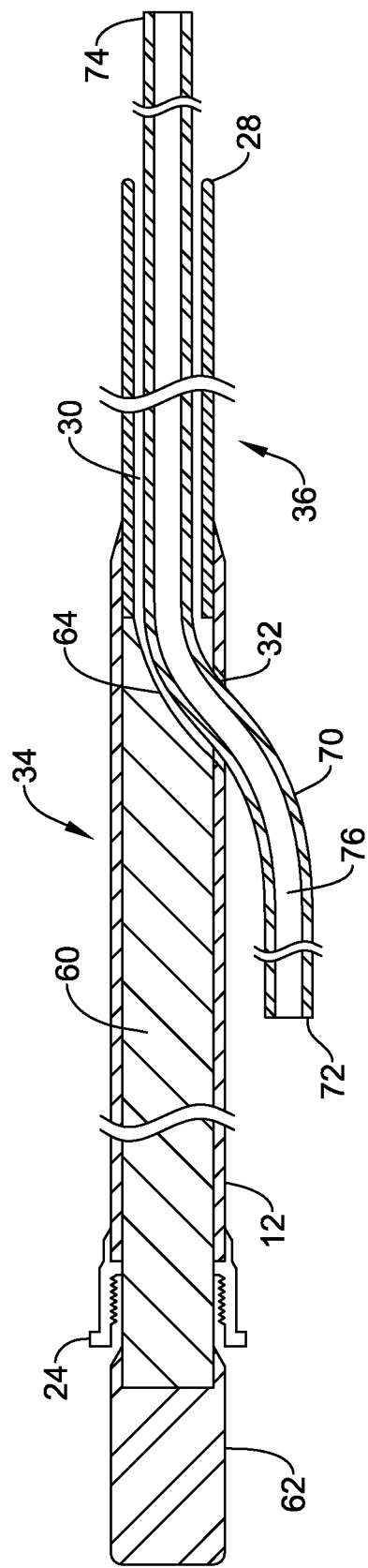
FIG. 8 is a longitudinal cross-sectional view illustrating accessories for use with the delivery catheter of the sent delivery system.

In some instances, the delivery catheter 12 may be provided with a guidewire loading stylet 60 and/or a guidewire loading sheath 70, as shown at FIG. 8, to assist a user in loading the guidewire 18 through the lumen 30 and out the guidewire port 32. For instance, the guidewire loading stylet 60 may be a tubular or solid elongate shaft configured to be inserted into the lumen 30 of the delivery catheter 12. The guidewire loading stylet 60 may include a handle portion 62 at the proximal end for manipulating the stylet 60 by a user and a ramp portion 64 having a curved or angled surface to facilitate directing a guidewire out through the guidewire port 32 from the lumen 30 of the delivery catheter 12. Thus, a guidewire 18 being advanced proximally through the lumen 30 in the distal portion 36 of the delivery catheter 12 may engage the ramp portion 64, which redirects the proximal end of the guidewire 18 away from the central longitudinal axis of the lumen 30 and out the guidewire port 32.

In some instances, the guidewire loading stylet 60 may be removed from the delivery catheter 12 once delivery catheter 12 has been loaded onto the guidewire 18 in a rapid-exchange manner. In other instances, the guidewire loading stylet 60 may remain positioned in the lumen 30 as the delivery catheter 12 is advanced distally through the vasculature along the guidewire 18 to provide additional support throughout the proximal portion 34 of the delivery catheter 12.

Additionally or alternatively, the guidewire loading sheath 70 may be provided with the delivery catheter 12 to facilitate loading the delivery catheter 12 onto the guidewire 18 in a rapid-exchange manner. The guidewire loading sheath 70 may include an elongate tubular member having a proximal end 72, a distal end 74 and a lumen 76 extending therethrough. The guidewire loading sheath 70 may extend from the distal opening of the lumen 30 at the distal end 28 of the delivery catheter 12, through the lumen 30 in the distal portion 36 of the delivery catheter 12, and out the guidewire port 32 such that a proximal portion of the guidewire loading sheath 70 extends proximal of the guidewire port 32 exterior of the delivery catheter 12 and a distal portion of the guidewire loading sheath 70 extends distal of the distal end 28 exterior of the delivery catheter 12.

The guidewire 18 may be advanced proximally through the lumen 76 of the guidewire loading sheath 70 from the distal end 74 and out the proximal end 72 of the guidewire loading sheath 70 in order to route the guidewire 18 out the guidewire port 32. In some instances, the distal end 74 of the guidewire loading sheath 70 may be flared outward, or provided with some other funnel structure to facilitate feeding the guidewire 18 into the lumen 76. After the guidewire 18 has been advanced through the distal portion 36 of the delivery catheter 12 and out the guidewire port 32, the guidewire loading sheath 70 may be removed. For example, the guidewire loading sheath 70 may be peeled off of the guidewire 18. In some instances, the guidewire loading sheath 70 may include a preferential tear line, slit, slot, perforations, thin wall, or weakened region extending longitudinally along the length of the guidewire loading sheath 70 along which the guidewire 18 may be pulled through to remove the guidewire loading sheath 70 from the guidewire 18.

Figure 9:
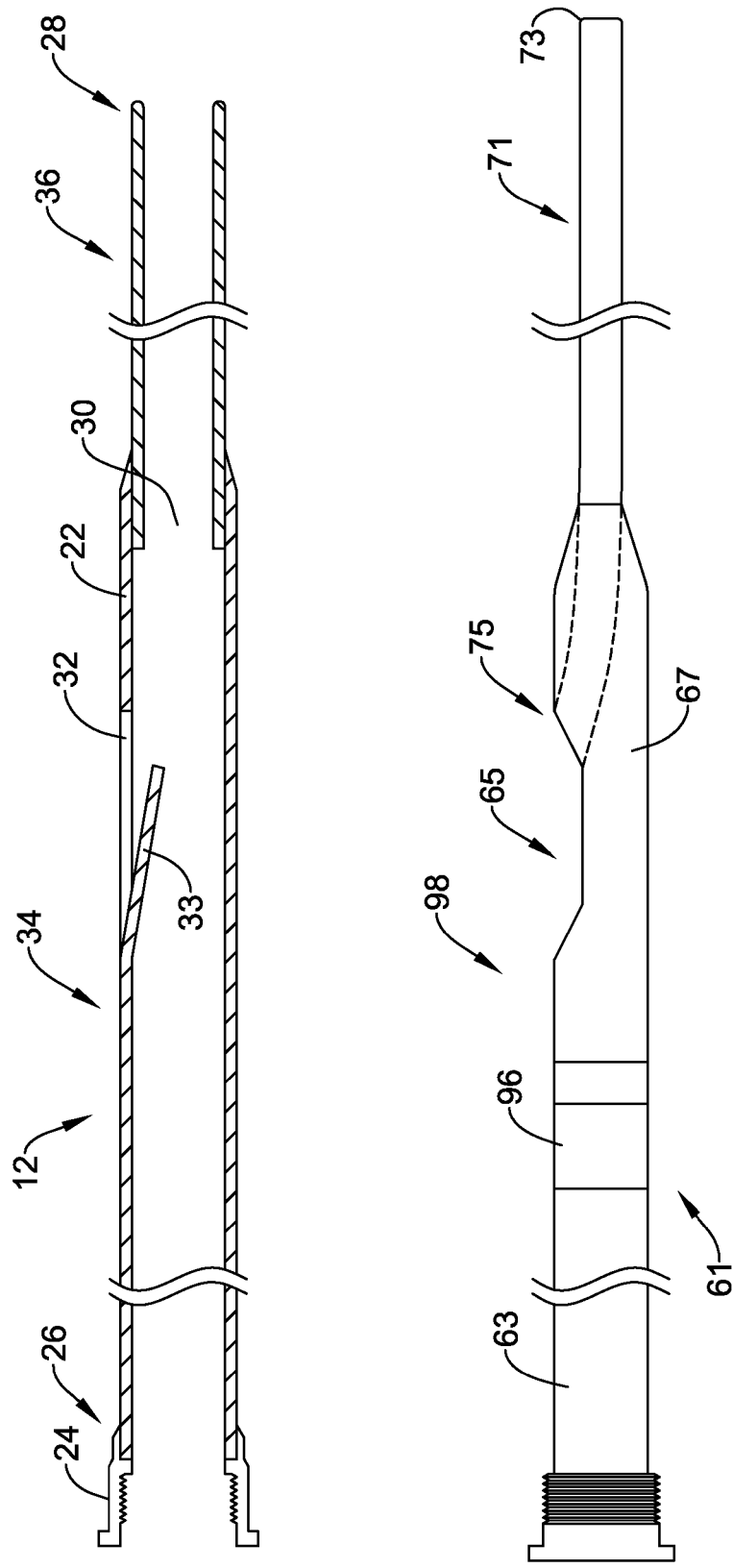
FIG. 9 illustrates components of another exemplary stent delivery system.

In instances where the stylet 60 and the guidewire loading sheath 70 are both used for guidewire loading, they may be joined together. For instance, as shown in FIG. 9, the stent delivery system 10 may include an integrated stylet and guidewire sheath 98 including a stylet portion 61 and a guidewire sheath portion 71. In this case, the integrated stylet/sheath 98 may remain in place in the lumen 30 of the delivery catheter 12 to provide support and a distal tip extending distal of the distal end 28 of the delivery catheter 12 which provides an eased diametric and stiffness transition to improve access of the system into tortuous anatomies.

The integrated stylet/sheath 98 may include a proximal stylet portion 61 sized to be inserted into the lumen 30 of the delivery catheter 12. The stylet portion 61 may include a proximal shaft 63 coupled to a distal tubular member, such as a hypotube 67 with a skived port 65 through a sidewall of the hypotube 67. The proximal shaft 63 may be solid or tubular and may be provided with a desired amount of stiffness to provide additional support throughout the proximal portion 34 of the delivery catheter 12. In some instances, the integrated stylet/sheath 98 may include a rotational coupling 96 between the proximal shaft 63 and the hypotube 67 to provide relative rotational movement between the proximal shaft 63 and the hypotube 67. The rotational coupling 96 may allow the skived port 65 to be aligned and remain aligned with the guidewire port 32 in the delivery catheter 12 during usage.

The integrated stylet/sheath 98 may include a lumen 69 into which the proximal portion of the guidewire sheath portion 71 extends into. The guidewire sheath portion 71 may be a tubular member having a lumen 77 extending therethrough from a distal end 73 to a proximal end 75 of the tubular member for receiving the guidewire 18 therethrough. The proximal end 75 of the guidewire sheath portion 71 may be positioned proximate the skived port 65 of the hypotube 67 such that a guidewire 18 extending through the lumen 77 of the guidewire sheath portion 71 may be directed out through the skived port 65 and the guidewire port 32 of the delivery catheter 12.

Figure 10:
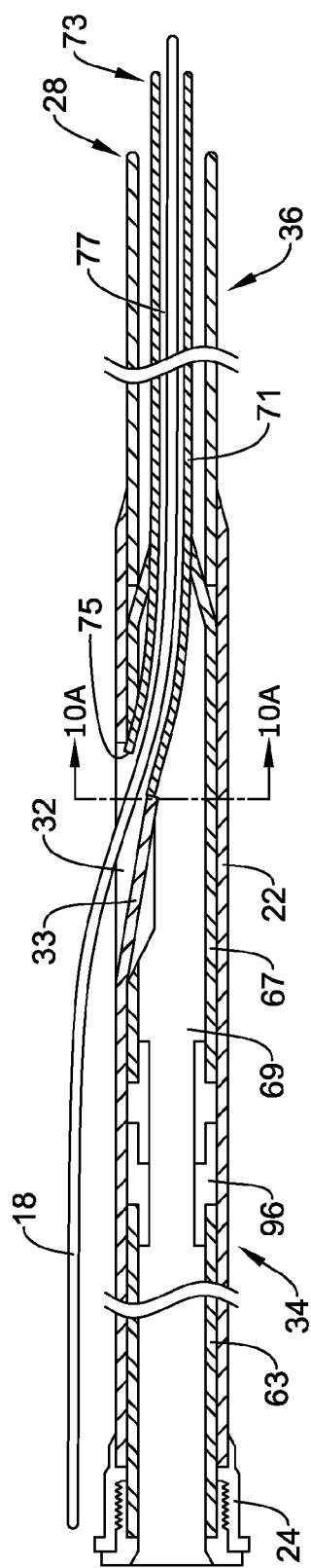
FIG. 10 is a longitudinal cross-sectional view illustrating the components of the exemplary stent delivery system of FIG. 9 in an assembled configuration.
Figure 10A:
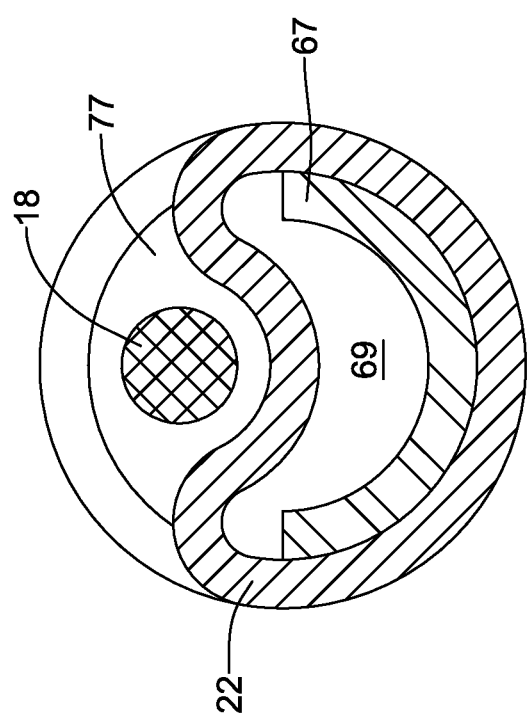
FIG. 10A is a transverse cross-sectional view taken along line 10A-10A of FIG. 10.

FIG. 10 illustrates the integrated stylet/sheath 98 inserted into the lumen 30 of the delivery catheter 12, with a guidewire 18 positioned through the guidewire sheath portion 71. As shown in FIGS. 9 and 10, the delivery catheter 12 may include a guidewire ramp 33 formed in the sidewall of the delivery catheter 12 proximate the guidewire port 32 which may substantially correlate with the proximal end 75 of the guidewire sheath portion 71 to provide a continuous trajectory for directing the guidewire 18 out of the skived port 65 and the guidewire port 32 of the delivery catheter 12. FIG. 10A is a cross-sectional view showing the guidewire 18 positioned exterior of the guidewire ramp 33, exiting the guidewire port 32 of the delivery catheter 12.

A distal portion of the guidewire sheath portion 71 may extend distal of the distal end 28 of the delivery catheter 12 to provide a stepped diametric and stiffness transition of the system to improve access of the system into tortuous anatomies. For example, the distally extending portion of the guidewire sheath portion 71 may be more flexible than the delivery catheter 12, thus enhancing the ability to navigate tortuous vasculatures.

With such a configuration, the delivery catheter 12 may be advanced through the vasculature to a target location while tracking over the guidewire 18 with the integrated stylet/sheath 98 positioned in the lumen 30 of the delivery catheter 12. Once properly positioned, the guidewire 18 may be removed proximally, followed by withdrawal of the integrated stylet/sheath 98 from the lumen 30 of the delivery catheter 12. Subsequent removal of the integrated stylet/sheath 98, the introducer sheath 14 may be advanced into the hub assembly 24 and through the lumen 30 of the delivery catheter 12 and the stent 20 may be deployed at the target location as described herein.

Figure 11:
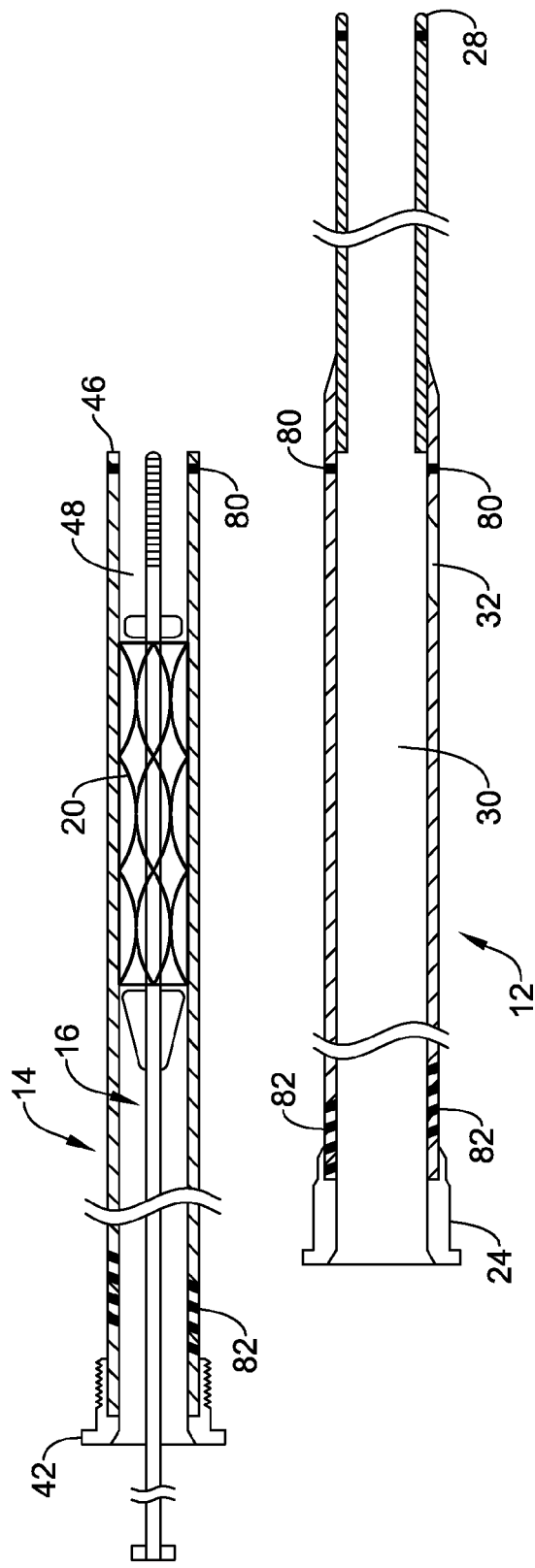
FIG. 11 is a longitudinal cross-sectional view of components of another exemplary stent delivery system.

As shown in FIG. 11, in some instances, the delivery catheter 12 and/or the introducer sheath 14 may include indicia, such as radiopaque markers or bands 80 and/or visual markers 82 which may be used to verify or confirm that the introducer sheath 14 has been sufficiently advanced into the lumen 30 of the delivery catheter 12 to ensure the distal end 46 of the introducer sheath 14 is advanced beyond the guidewire port 32 prior to advancing the stent 20 through the delivery system 10. For example, the introducer sheath 14 may include a visual marker 82 proximate the proximal end of the introducer sheath 14. A reference point of the visual marker 82 of the introducer sheath 14 may be aligned with a reference point of the delivery catheter 12 (e.g., a visual marker 82 of the delivery catheter 12 and/or proximal end of the hub assembly 24 of the delivery catheter 12) to indicate to a user that the introducer sheath 14 has been advanced beyond the guidewire port 32. For example, alignment of the distal end of the visual marker 82 of the introducer sheath 14 with the proximal end of the hub assembly 24 of the delivery catheter 12 may be indicative to a user that the introducer sheath 14 has been advanced beyond the guidewire port 32.

Alternatively or additionally, the delivery catheter 12 and the introducer is sheath 14 may include radiopaque markers 80 which may be aligned to indicate to a user that the introducer sheath 14 has been advanced beyond the guidewire port 32. For example, the delivery catheter 12 may include a radiopaque marker 80 distal of the guidewire port 32 and the introducer sheath 14 may include a radiopaque marker 80 proximate the distal end 46 of the introducer sheath 14. Alignment of the radiopaque marker 80 of the introducer sheath 14 with the radiopaque marker 80 of the hub assembly 24 of the delivery catheter 12 using a fluoroscopic technique or other imaging technique to visualize the relative position of the components during a medical procedure may be indicative to a user that the introducer sheath 14 has been advanced beyond the guidewire port 32.

Figure 12:
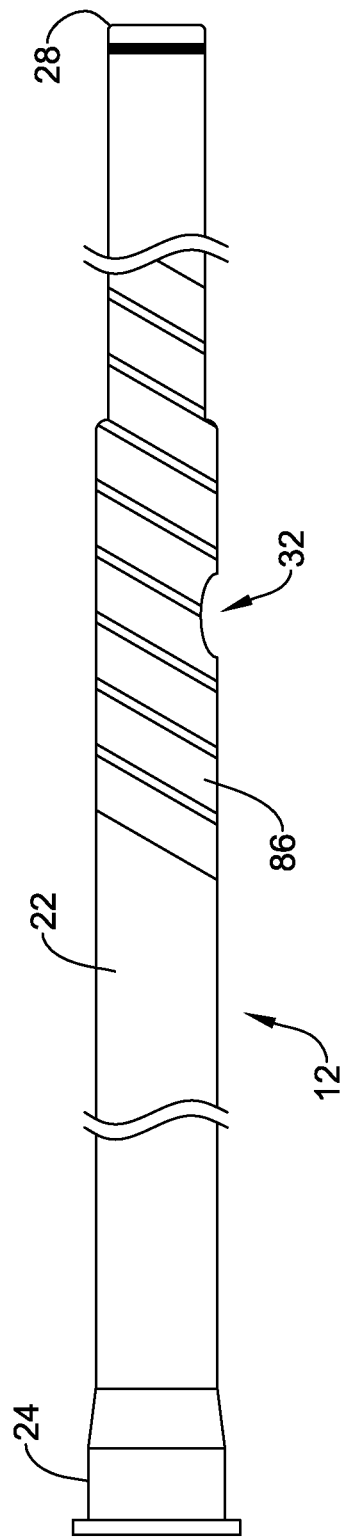
FIG. 12 illustrates an exemplary reinforcement structure of a delivery catheter of the stent delivery system.

In some instances, the delivery catheter 12 may include a reinforcement member 86 positioned proximate the guidewire port 32 such as shown in FIG. 12. For instance, the reinforcement member 86 may span the guidewire port 32 and extend proximally and/or distally of the guidewire port 32. The reinforcement member 86 may help strengthen the elongate shaft 22 of the delivery catheter 12 at the guidewire port 32 and/or provide kink resistance proximate the guidewire port 32. In some instances, the reinforcement member 86 may be a tubular member such as a braided or coiled member, or a laser cut or micromachined hypotube having one or more, or a plurality of slots (such as perpendicular or helical slots) formed therein to enhance the flexibility of the reinforcement member 86. In some instances, the reinforcement member 86 may be positioned interior of a polymeric tubular member of the delivery catheter 12, exterior of a polymeric tubular member of the delivery catheter 12, or interposed between inner and outer layers of polymeric material of the delivery catheter 12. The reinforcement member 86 may include a side opening extending through the sidewall of the reinforcement member 86 which is aligned with the guidewire port 32.

Figure 13A:
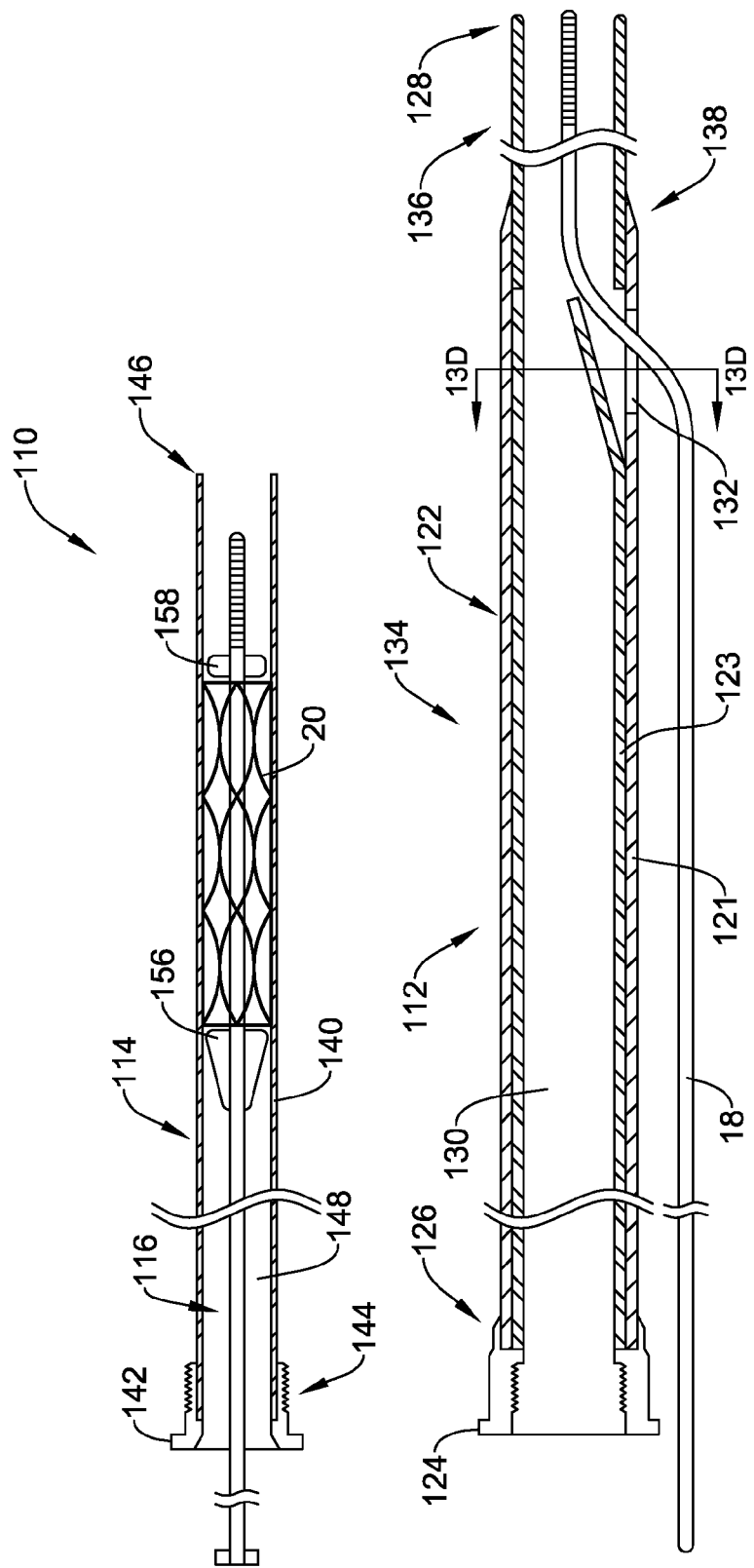
FIGS. 13A-13E illustrate another configuration of an exemplary stent delivery system.

Components of another exemplary stent delivery system 110 for delivering a stent, or other prosthetic device to a target location of a body lumen, such as a blood vessel or a biliary duct are shown in FIG. 13A. The stent delivery system 110 may include a delivery catheter 112, such as a microcatheter dimensioned to reach remote locations of a vasculature, configured to deliver a stent 20 to a target location, such as an occlusion in a blood vessel. The delivery catheter 112 may include an elongate shaft 122 is extending distally from a hub assembly 124. The elongate shaft 122 may have a proximal end 126 and a distal end 128, with a lumen 130 extending therethrough in fluid communication with the hub assembly 124. Thus, the lumen 130 may extend the entire length of the delivery catheter 112 from the hub assembly 124 to the distal end 128 of the elongate shaft 122. The delivery catheter 112 may include a single lumen (e.g., only the lumen 130), thus reducing the profile of the delivery catheter 112 relative to catheters having multiple lumens extending therethrough. The lumen 130 may extend axially through the elongate shaft 122 centered along a central longitudinal axis of the elongate shaft 122.

The delivery catheter 112 may include a guidewire port 132 located intermediate the proximal end 126 and the distal end 128 of the elongate shaft 122 providing the delivery catheter 112 with "rapid-exchange" capabilities. The guidewire port 132 may be located a relatively short distance from the distal end 128 and a relatively long distance from the proximal end 126 of the elongate shaft 122 of the delivery catheter 112. In some instances, the elongate shaft 122 may have a length in the range of about 80 cm to about 150 cm, with the guidewire port 132 located about 15 cm to about 35 cm proximal of the distal end 128. The guidewire port 132 may extend through a sidewall of the elongate shaft 122, providing access to the lumen 130 from exterior of the elongate shaft 122. Thus, the delivery catheter 112 may be advanced over a guidewire 18 which extends through the lumen 130 of the elongate shaft 122 between the guidewire port 132 and the distal end 128 of the elongate shaft 122, and external of the elongate shaft 122 proximal of the guidewire port 132 in a rapid exchange manner.

The elongate shaft 122 may include one or more, or a plurality of regions along the length of the elongate shaft 122 having different configurations and/or characteristics. For example, the elongate shaft 122 may include a proximal portion 134 and a distal portion 136 extending distal of the proximal portion 134. In some embodiments, the distal portion 136 may have an outer diameter less than the outer diameter of the proximal portion 134 to reduce the profile of the distal portion of the elongate shaft 122 and facilitate navigation in tortuous vasculature. Furthermore, the distal portion 136 may be more flexible than the proximal portion 134. The portion of the lumen 130 extending through the proximal portion 134 may be coaxial with the portion of the lumen 130 extending through the distal portion 136. The elongate shaft 122 may include a transition region 138 between the proximal portion 134 and the distal portion 136. The guidewire port 132 may be located proximal of the transition region 138, thus located in the proximal portion 134 of the elongate shaft 122.

The elongate shaft 122 may include an outer tubular member 121 and a collapsible sheath 123 positioned interior of the outer tubular member 121. A distal portion of the collapsible sheath 123 may extend across the guidewire port 132, which extends through a sidewall of the outer tubular member 121. As shown in FIG. 13D, the collapsible sheath 123 may be sufficiently flexible to deflect the distal portion of the collapsible sheath 123 radially inward away from the guidewire port 132 to allow a guidewire 18 to pass through the guidewire port 132 from the lumen 130 distal of the guidewire port 132 to a location proximal of the guidewire port 132 exterior thereto. Thus, the guidewire 18 may be directed exterior of the collapsible sheath 123 and out the guidewire port 132. When positioned through the distal portion of the delivery catheter 112, the guidewire 18 may extend between the outer tubular member 121 and the collapsible sheath 123 distal of the guidewire port 132 such that the guidewire 18 is not positioned interior of the collapsible sheath 123. When the guidewire 18 is not positioned in the guidewire port 132, the distal portion of the collapsible sheath 123 may be moved against the outer tubular member 121, closing off the guidewire port 132 from the lumen 130 of the delivery catheter 112.

The stent delivery system 110 may also include a sheath, such as an introducer sheath 114 for retaining the stent 20 in a radially compressed configuration for delivery to the target location. The introducer sheath 114 may include an elongate shaft 140 extending distally from a hub assembly 142. The elongate shaft 140 may have a proximal end 144 and a distal end 146, with a lumen 148 extending therethrough in fluid communication with the hub assembly 142. The elongate shaft 140 may be formed of any suitable materials, including those listed above.

The stent delivery system 110 may additionally include a delivery wire 116, similar to that described above regarding the stent delivery system 10, extendable through the lumen 130 of the delivery catheter 112 for deploying a stent 20 from the distal end 128 of the delivery catheter 112.

The stent 20 may be a self-expanding stent configured to automatically expand from a radially compressed configuration when radially constrained to a radially expanded configuration when unconstrained. The stent 20 may be formed from any number of biocompatible materials, including polymeric materials, metals, and metal alloys, such as stainless steel, tantalum, or a nickel titanium alloy such as a superelastic nickel titanium alloy known as Nitinol.

The stent 20 may be pre-loaded in the introducer sheath 114 between the proximal bumper 156 and the distal bumper 158 of the delivery wire 116 in a radially compressed configuration prior to use with the introducer sheath 114 constraining the stent 20 in the radially compressed configuration. In other embodiments the stent 20 may be pre-loaded in another sheath and then inserted into the introducer sheath 114 during the medical procedure or radially compressed and then inserted into the introducer sheath 114 during the medical procedure. Alternatively, the stent 20 may be inserted directly into the lumen 130 of the delivery catheter 12 during the medical procedure without the use of the introducer sheath 114.

The stent 20 may be pushed distally through the lumen 148 of the introducer sheath 114 by manipulating the delivery wire 116 such that the proximal bumper 156 contacts the stent 20 and urges the stent 20 distally. If it is desired to pull the stent 20 proximally, the delivery wire 116 may be manipulated proximally such that the distal bumper 158 contacts the stent 20 and urges the stent 20 proximally.

Figure 13B:
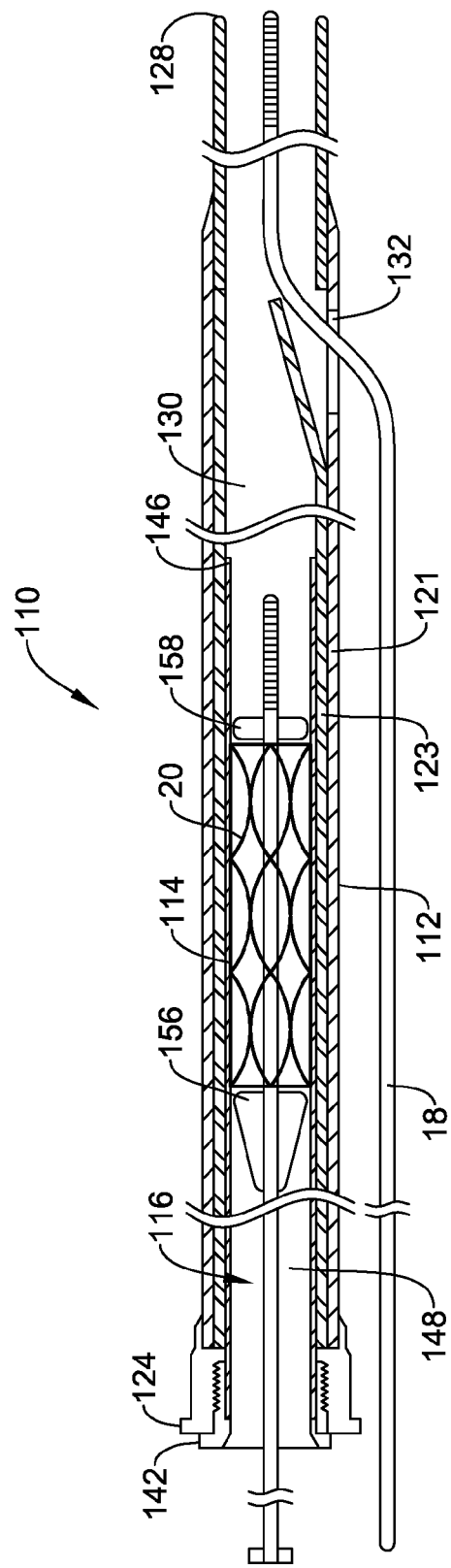

Turning to FIG. 13B, the elongate shaft 140 of the introducer sheath 114 may be sized to be inserted into the lumen 130 of the delivery catheter 112 through the hub assembly 124 of the delivery catheter 112. For instance, the introducer sheath 114 may be slidably disposed in the lumen 130 of the delivery catheter 112.

In some instances, the hub assembly 142 of the introducer sheath 114 may be configured to engage and/or be coupled to the hub assembly 124 of the delivery catheter 112 when the introducer sheath 114 is fully advanced through the lumen 130 or provided with complementary indicia, as described above, in order to provide an operator with verification or confirmation that the introducer sheath 114 is sufficiently advanced into the delivery catheter 112.

Figure 13C:
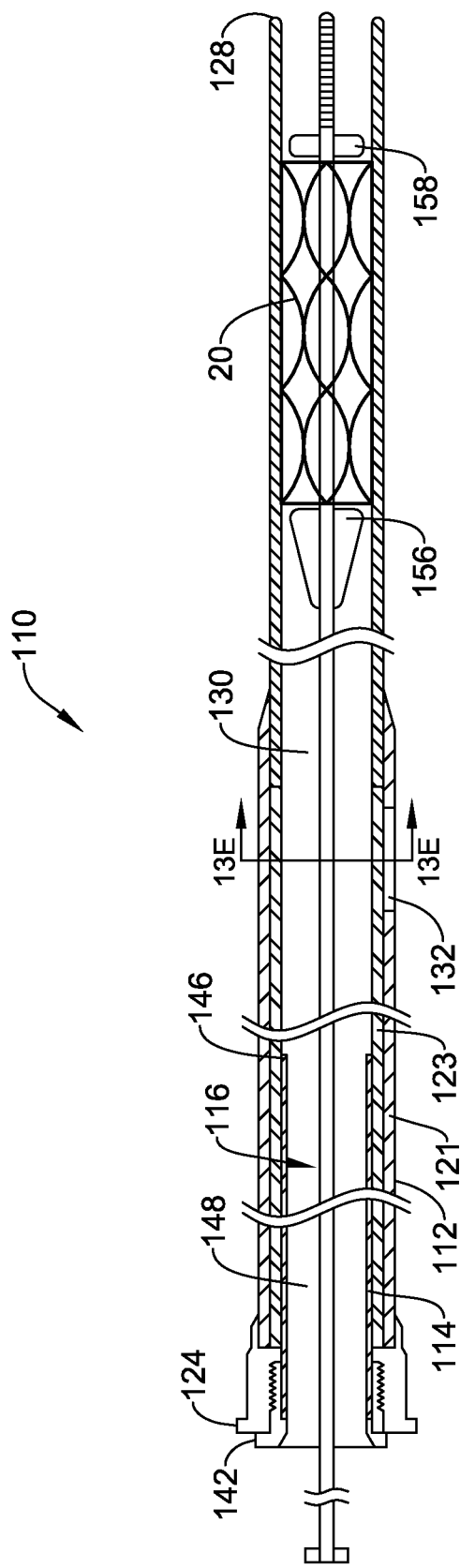
Figures 13D, 13E:
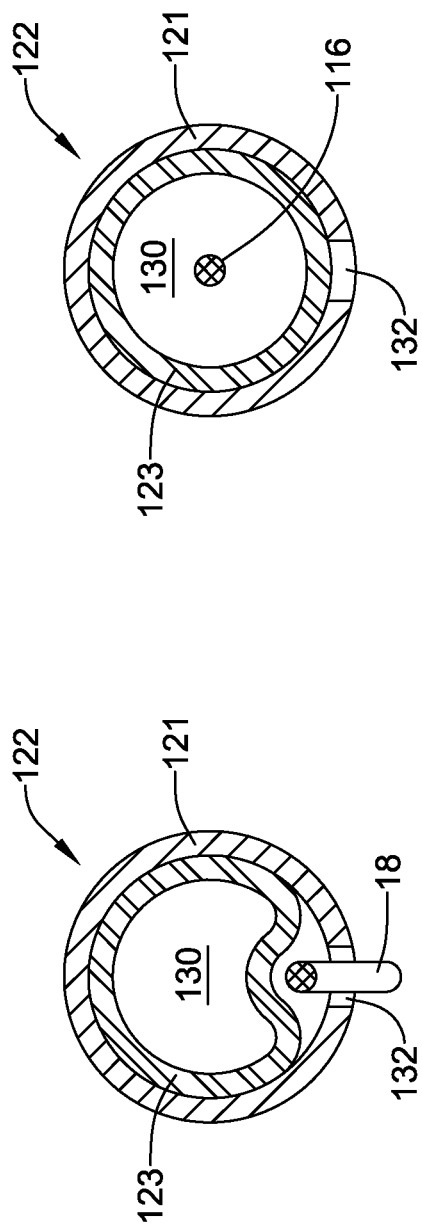

As shown in FIG. 13C, when the guidewire 18 is removed from the lumen 130 of the delivery catheter 112, the distal portion of the collapsible sheath 123 may move radially outward toward the outer tubular member 121 proximate the guidewire port 132. Thus, as shown in FIG. 13E, with the guidewire 18 removed from the guidewire port 132, the collapsible sheath 123 may extend across the guidewire port 132 to close off the guidewire port 132 to allow the stent 20 to be passed through the lumen 130 of the delivery catheter 112 from proximal of the guidewire port 132 to distal of the guidewire port 132 without the guidewire port 132 interfering with advancement or retraction of the stent 20 past the guidewire port 132. Thus, the delivery wire 116 with the stent 20 mounted thereon, may be advanced past the guidewire port 132 with the delivery wire 116 and stent 20 positioned interior of the collapsible sheath 123.

Figure 14A:
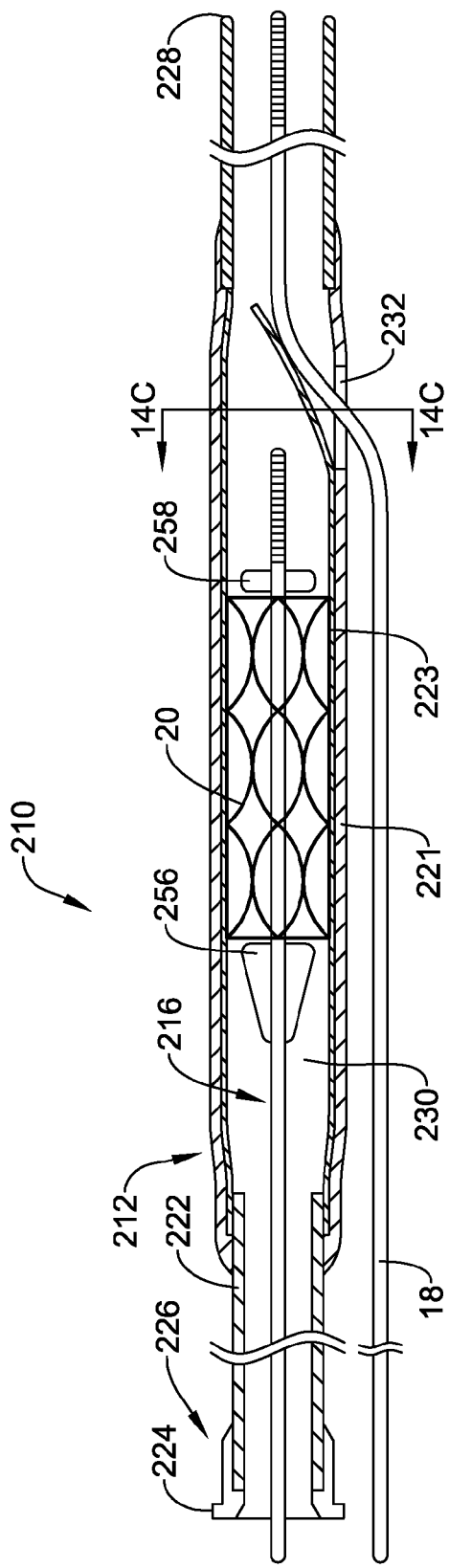
FIGS. 14A-14D illustrate yet another configuration of an exemplary stent delivery system.

FIG. 14A illustrates another embodiment of a stent delivery system 210 for delivering a stent, or other prosthetic device to a target location of a body lumen, such as a blood vessel or a biliary duct. In this embodiment, a stent 20 may be pre-loaded in the lumen 230 of the delivery catheter 212 prior to advancing the delivery catheter 212 through the vasculature of a patient.

The delivery catheter 212 may include an elongate shaft 222 extending distally from a hub assembly 224. The elongate shaft 222 may have a proximal end 226 and a distal end 228, with a lumen 230 extending therethrough in fluid communication with the hub assembly 224. Thus, the lumen 230 may extend the entire length of the delivery catheter 212 from the hub assembly 224 to the distal end 228 of the elongate shaft 222. The delivery catheter 212 may include a single lumen (e.g., only the lumen 230), thus reducing the profile of the delivery catheter 212 relative to catheters having multiple lumens extending therethrough. The lumen 230 may extend axially through the elongate shaft 222 centered along a central longitudinal axis of the elongate shaft 222.

The delivery catheter 212 may include a guidewire port 232 located intermediate the proximal end 226 and the distal end 228 of the elongate shaft 222 providing the delivery catheter 212 with "rapid-exchange" capabilities. The guidewire is port 232 may be located a relatively short distance from the distal end 228 and a relatively long distance from the proximal end 226 of the elongate shaft 222 of the delivery catheter 212. In some instances, the elongate shaft 222 may have a length in the range of about 80 cm to about 150 cm, with the guidewire port 232 located about 15 cm to about 35 cm proximal of the distal end 228. The guidewire port 232 may extend through a sidewall of the elongate shaft 222, providing access to the lumen 230 from exterior of the elongate shaft 222. Thus, the delivery catheter 212 may be advanced over a guidewire 18 which extends through the lumen 230 of the elongate shaft 222 between the guidewire port 232 and the distal end 228 of the elongate shaft 222, and external of the elongate shaft 222 proximal of the guidewire port 232 in a rapid exchange manner.

The elongate shaft 222 may include an outer tubular member 221 and a collapsible sheath 223 positioned interior of the outer tubular member 221. A distal portion of the collapsible sheath 223 may extend across the guidewire port 232, which extends through a sidewall of the outer tubular member 221. As shown in FIG. 14C, the collapsible sheath 223 may be sufficiently flexible to deflect the distal portion of the collapsible sheath 223 radially inward away from the guidewire port 232 to allow a guidewire to pass through the guidewire port 232 from the lumen 230 distal of the guidewire port 232 to a location proximal of the guidewire port 232 exterior thereto. Thus, the guidewire 18 may be directed exterior of the collapsible sheath 223 and out the guidewire port 232. When positioned through the distal portion of the delivery catheter 212, the guidewire 18 may extend between the outer tubular member 221 and the collapsible sheath 223 distal of the guidewire port 232 such that the guidewire 18 is not positioned interior of the collapsible sheath 223. When the guidewire 18 is not positioned in the guidewire port 232, the distal portion of the collapsible sheath 223 may be moved against the outer tubular member 221, closing off the guidewire port 232 from the lumen 230 of the delivery catheter 212.

The stent delivery system 210 may additionally include a delivery wire 216, similar to that described above regarding the stent delivery system 10, extendable through the lumen 230 of the delivery catheter 212 for deploying a stent 20 from the distal end 228 of the delivery catheter 212.

The stent 20 may be a self-expanding stent configured to automatically expand from a radially compressed configuration when radially constrained to a radially expanded configuration when unconstrained. The stent 20 may be formed from any number of biocompatible materials, including polymeric materials, metals, and metal alloys, such as stainless steel, tantalum, or a nickel titanium alloy such as a superelastic nickel titanium alloy known as Nitinol.

The stent 20 may be pre-loaded in the delivery catheter 212 between the proximal bumper 256 and the distal bumper 258 of the delivery wire 216 in a radially compressed configuration prior to use with the delivery catheter 212 constraining the stent 20 in the radially compressed configuration. The stent 20 may be pre-loaded in the delivery catheter 212 at a location proximal of the guidewire port 232 such that the guidewire 18 does not extend through the stent 20 when the delivery catheter 212 is being advanced along the guidewire 18 in a rapid-exchange manner.

The stent 20 may be pushed distally by manipulating the delivery wire 216 such that the proximal bumper 256 contacts the stent 20 and urges the stent 20 distally. If it is desired to pull the stent 20 proximally, the delivery wire 216 may be manipulated proximally such that the distal bumper 258 contacts the stent 20 and urges the stent 20 proximally.

Figure 14B:
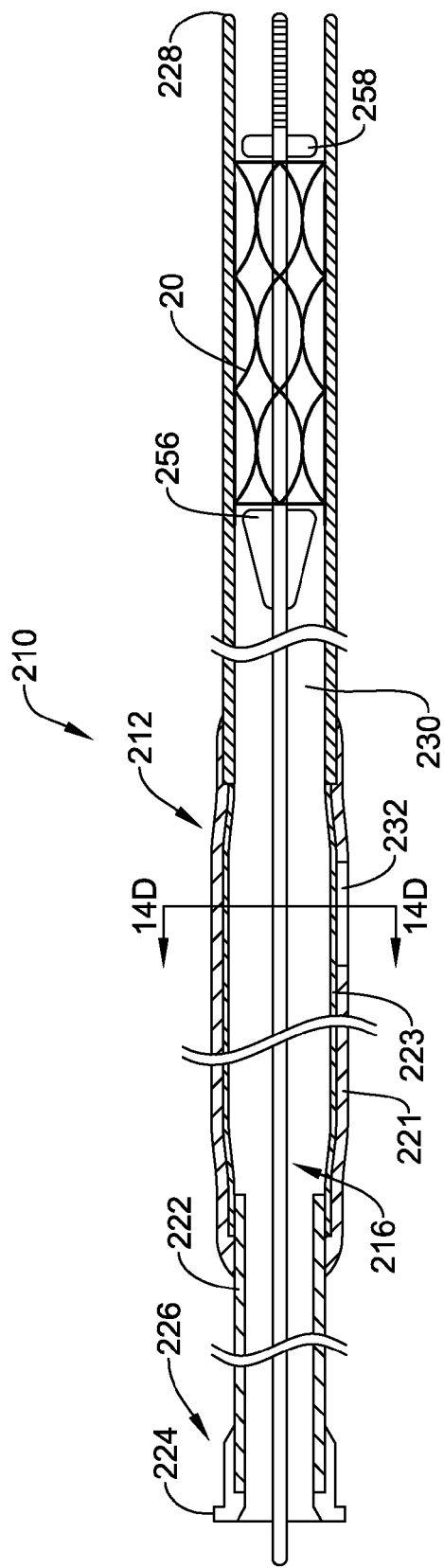
Figure 14C:
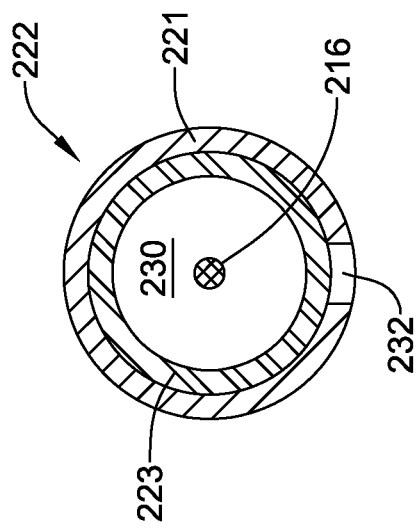
Figure 14D:
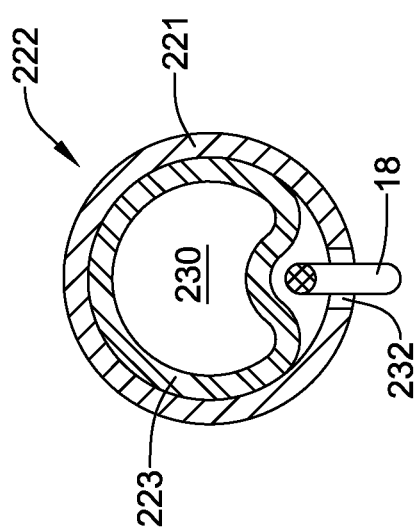

As shown in FIG. 14B, when the guidewire 18 is removed from the lumen 230 of the delivery catheter 212, the distal portion of the collapsible sheath 223 may move radially outward toward the outer tubular member 221 proximate the guidewire port 232. Thus, as shown in FIG. 14D, with the guidewire 18 removed from the guidewire port 232, the collapsible sheath 223 may extend across the guidewire port 232 to close off the guidewire port 232 to allow the stent 20 to be passed through the lumen 230 of the delivery catheter 212 from proximal of the guidewire port 232 to distal of the guidewire port 232 without the guidewire port 232 interfering with advancement or retraction of the stent 20 past the guidewire port 232. Thus, the delivery wire 216 with the stent 20 mounted thereon, may be advanced past the guidewire port 232 with the delivery wire 216 and stent 20 positioned interior of the collapsible sheath 223.

The stent delivery systems for delivering a self-expanding stent to a target location described herein may benefit from having rapid-exchange capabilities, while providing the delivery catheter with enhanced distal flexibility and/or maneuverability for reaching remote and/or tortuous locations in the vasculature.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A stent delivery system, comprising:
   a delivery catheter, comprising
      an elongate shaft extending distally from a hub assembly, the elongate shaft defining a lumen extending therethrough from a proximal end of the elongate shaft to a distal end of the elongate shaft, the elongate shaft further defining a guidewire port in a sidewall thereof, the guidewire port providing access to the lumen at a location between the proximal and distal ends of the elongate shaft, and
      an inwardly deflectable member extending across the guidewire port, the deflectable member configured to close the guidewire port when a guidewire is not extending therethrough, so as to allow a stent to be passed through the shaft lumen without interference from the guidewire port; and
   a stent introducer sheath slidably disposed in the lumen of the elongate delivery catheter shaft.

2. The stent delivery system of claim 1, further comprising:
   a guidewire configured to extend through the guidewire port and down the lumen of the elongate shaft distal of the guidewire port; and
   a delivery wire having a stent disposed on a distal portion thereof, the delivery wire configured to be passed through the introducer sheath from proximal of the guidewire port to distal of the guidewire port into the lumen of the elongate shaft.

3. The stent delivery system of claim 1, wherein a proximal end of the introducer sheath is located proximal of the hub assembly of the delivery catheter, and wherein a distal end of the introducer sheath is located distal of the guidewire port.

4. The stent delivery system of claim 3, the introducer sheath comprising a introducer sheath hub assembly disposed on the proximal end thereof, wherein the introducer sheath hub assembly is configured to engage with the hub assembly of the delivery catheter.

5. The stent delivery system of claim 1, wherein the inwardly deflectable member is collapsible away from the guidewire port to open the guidewire port to the lumen in order to allow a guidewire to be passed through the guidewire port.

6. The stent delivery system of claim 1, wherein the delivery catheter includes a single lumen for receiving either:
   a) a guidewire extending through the guidewire port, the single lumen of the elongate shaft, and the distal end of the elongate shaft, and external of the elongate shaft proximal of the guidewire port; or
   b) a delivery wire having a stent disposed on a distal portion thereof, the delivery wire extending through a proximal end of the elongate shaft, the single lumen of the elongate shaft, and a distal end of the elongate shaft.

7. The stent delivery system of claim 1, wherein the inwardly deflectable member is a sheath disposed concentrically within the elongate shaft, wherein an outer surface of the inwardly deflectable member is disposed adjacent an inner surface of the elongate shaft.

8. A stent delivery system having rapid exchange capabilities, the stent delivery system comprising:
   a delivery catheter, comprising
      an elongate shaft extending distally from a hub assembly, the elongate shaft defining a lumen extending therethrough from a proximal end of the elongate shaft to a distal end of the elongate shaft, the elongate shaft further defining a guidewire port extending through a sidewall thereof at a location between the proximal and distal ends of the elongate shaft, wherein the guidewire port is configured to provide access to the lumen for advancement of the delivery catheter over a guidewire extending through the lumen between the guidewire port and the distal end of the elongate shaft and external of the elongate shaft proximal of the guidewire port, and
      an inwardly deflectable member extending across the guidewire port, the deflectable member configured to close the guidewire port when a guidewire is not extending therethrough, so as to allow a stent to be passed through the shaft lumen without interference from the guidewire port; and
   a stent introducer sheath slidably disposed in the lumen of the elongate shaft.

9. The stent delivery system of claim 8, wherein the stent delivery system further comprises:
   a guidewire configured to extend through the guidewire port and down the lumen of the elongate shaft distal of the guidewire port; and
   a delivery wire having a stent disposed on a distal portion thereof, the delivery wire being configured to be passed through the introducer sheath from proximal of the guidewire port to distal of the guidewire port into the lumen of the elongate shaft.

10. The stent delivery system of claim 8, wherein the introducer sheath includes a stent disposed therein at a position proximal of the guidewire port.

11. The stent delivery system of claim 10, wherein the introducer sheath is slidably disposed in the lumen of the elongate shaft of the delivery catheter.

12. The stent delivery system of claim 11, wherein the introducer sheath includes an introducer sheath hub assembly disposed at least partially proximal of the hub assembly of the delivery catheter.

13. The stent delivery system of claim 8, wherein the inwardly deflectable member is a sheath disposed concentrically within the elongate shaft, wherein an outer surface of the inwardly deflectable member is disposed adjacent an inner surface of the elongate shaft.

14. A stent delivery system, comprising:
a delivery catheter, comprising
an inner sheath defining a lumen, wherein a distal end of the inner sheath is deflectable in a radially inward direction,
an outer tubular member disposed concentrically around the inner sheath, the outer tubular member defining a guidewire port in a sidewall thereof, wherein the guidewire port overlies the distal end of the inner sheath, and
a hub assembly attached to a proximal end of the outer tubular member; and
an introducer sheath slidably disposed in the lumen of the inner sheath,
wherein the distal end of the inner sheath is configured to deflect away from the outer tubular member to enable fluid communication between the guidewire port and the lumen of the inner sheath, and
wherein the distal end of the inner sheath is also configured to deflect toward the guidewire port to close the guidewire port, thereby allowing a stent to be passed through the lumen of the inner sheath without interference from the guidewire port.

* * * * *